US012699046B2

(12) United States Patent
Nakamura

(10) Patent No.: US 12,699,046 B2
(45) Date of Patent: Aug. 4, 2026

(54) LASER GAS ANALYZER

(71) Applicant: Yokogawa Electric Corporation, Tokyo (JP)

(72) Inventor: Hajime Nakamura, Tokyo (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 275 days.

(21) Appl. No.: 18/131,047

(22) Filed: Apr. 5, 2023

(65) Prior Publication Data

US 2023/0314311 A1     Oct. 5, 2023

(30) Foreign Application Priority Data

Apr. 5, 2022     (JP) ................................. 2022-062873

(51) Int. Cl.
*G01N 21/31*          (2006.01)
*G01N 21/01*          (2006.01)
(Continued)

(52) U.S. Cl.
CPC ............. *G01N 21/31* (2013.01); *G01N 21/01* (2013.01); *G01N 21/39* (2013.01);
(Continued)

(58) Field of Classification Search
CPC ............... G01N 21/31; G01N 33/0027; G01N 2201/06113; G01N 2201/062;
(Continued)

(56)          References Cited

U.S. PATENT DOCUMENTS 6,067,840 A *   5/2000   Chelvayohan ..... G01N 21/3504
                                                        250/343
7,352,463 B2 *  4/2008   Bounaix ................ G01N 21/61
                                                        356/437
(Continued)

FOREIGN PATENT DOCUMENTS

CN          202994654 U       6/2013
CN          111060199 A       4/2020
(Continued)

OTHER PUBLICATIONS

Yu-Kai He et al., "A Novel Carbon Monoxide Detection System Based on Infrared Absorption Used in Mine", Proceeding of the Fifth International Conference on Machine Learning and Cybernetics, Dalian, Aug. 13-16, 2006, pp. 645-649 (5 pages).
(Continued)

*Primary Examiner* — Dominic J Bologna
(74) *Attorney, Agent, or Firm* — Osha Bergman Watanabe & Burton LLP

(57)          ABSTRACT

A laser gas analyzer includes: a laser diode that irradiates a measurement target gas with laser light; a photodiode that receives the laser light that has passed through the measurement target gas; a processor that calculates a concentration of a component contained in the measurement target gas based on an amount of light of the laser light received by the photodiode; and a light emitting diode (LED) that irradiates LED light such that the LED light is received by the photodiode without passing through the measurement target gas.

3 Claims, 8 Drawing Sheets

(51) Int. Cl.
    *G01N 21/3504*     (2014.01)
    *G01N 21/39*     (2006.01)
    *G01N 33/00*     (2006.01)

(52) U.S. Cl.
    CPC ..... *G01N 33/0027* (2013.01); *G01N 21/3504*
    (2013.01); *G01N 2021/399* (2013.01); *G01N*
    *2201/06113* (2013.01); *G01N 2201/062*
    (2013.01)

(58) Field of Classification Search
    CPC ......... G01N 21/3504; G01N 2021/399; G01N
    21/39; G01N 21/01
    See application file for complete search history.

(56)           References Cited

U.S. PATENT DOCUMENTS

| | | | |
|---|---|---|---|
| 2006/0119851 | A1 | 6/2006 | Bounaix |
| 2007/0007449 | A1* | 1/2007 | Hubner .............. G01N 21/3504 |
| | | | 250/338.1 |

| | | | | |
|---|---|---|---|---|
| 2012/0212744 | A1 | 8/2012 | Okada | |
| 2019/0316965 | A1* | 10/2019 | Kobayashi .............. G01J 3/021 |
| 2020/0363265 | A1* | 11/2020 | Okada ................... G01J 3/0205 |
| 2023/0124208 | A1* | 4/2023 | Deguchi ........... G01N 21/3504 |
| | | | | 356/437 |

FOREIGN PATENT DOCUMENTS

| | | | |
|---|---|---|---|
| JP | H06-205851 | A | 7/1994 |
| JP | 2008-134076 | A | 6/2008 |
| RU | 2710083 | C1 | 12/2019 |

OTHER PUBLICATIONS

Extended European search report issued in corresponding European Applicaiton No. 23166591.0 dated Aug. 22, 2023 (5 pages).
Notice of Reasons for Refusal issued in corresponding Japanese Patent Application No. 2022-062873, dated Mar. 5, 2024 (6 pages).
First Office Action issued in related Chinese Application No. 202310363937.4 dated Feb. 2, 2026 (13 pages).

\* cited by examiner

LASER GAS ANALYZER

CROSS REFERENCE TO RELATED APPLICATION

The present application claims priority to Japanese patent application No. 2022-062873 filed on Apr. 5, 2022. The contents of this application are incorporated herein by reference in their entirety.

BACKGROUND

Technical Field

The present invention relates to a laser gas analyzer.

Description of the Related Art

A laser gas analyzer irradiates a measurement target gas with a laser light in a specific wavelength range, measures an amount of light of laser light that has passed through the measurement target gas, and calculates an attenuation of the laser light in the specific wavelength range to calculate a concentration of a component contained in the measurement target gas (for example, JP 2008-134076 A).

There is a laser gas analyzer that makes determination as failure of a light receiving unit when the light receiving unit of laser light does not perform output in response to the laser light while the light receiving unit is irradiated with laser light. However, in the laser gas analyzer described in JP 2008-134076 A, a light receiving element does not output or the output becomes extremely small in a case where an obstacle, such as powder dust, that blocks an optical path for laser light is present by a certain amount or more in a measurement target gas, and it causes a possibility of determination as failure of the light receiving element. Thus, the configuration of the laser gas analyzer in JP 2008-134076 A failed to accurately determine failure of the light receiving element.

SUMMARY

One or more embodiments provide a laser gas analyzer that allows accurately determining failure of a light receiving unit.

A laser gas analyzer of one or more embodiments includes a first irradiation unit (a laser diode), a light receiving unit (a photodiode), a calculation unit (a processor), and a second irradiation unit (an LED). The first irradiation unit irradiates a measurement target gas with laser light. The light receiving unit receives the laser light that has passed through the measurement target gas. The calculation unit calculates a concentration of a component contained in the measurement target gas based on an amount of light of the laser light received by the light receiving unit. The second irradiation unit irradiates light (LED light) such that the light is received by the light receiving unit without passing through the measurement target gas.

One or more embodiments can accurately determine failure of the light receiving unit.

BRIEF DESCRIPTION OF THE DRAWINGS

FIG. 1 is a block diagram of a laser gas analyzer according to Example 1;
FIG. 2 is a drawing illustrating light emission timings of a laser diode and a LED of Example 1;

FIG. 4 is a drawing illustrating light emission timings of a laser diode and a LED of Example 2;
FIG. 7 is a drawing illustrating a light emission timing of a laser diode of Comparative Example.

DESCRIPTION OF THE EMBODIMENTS

Figure 3A:
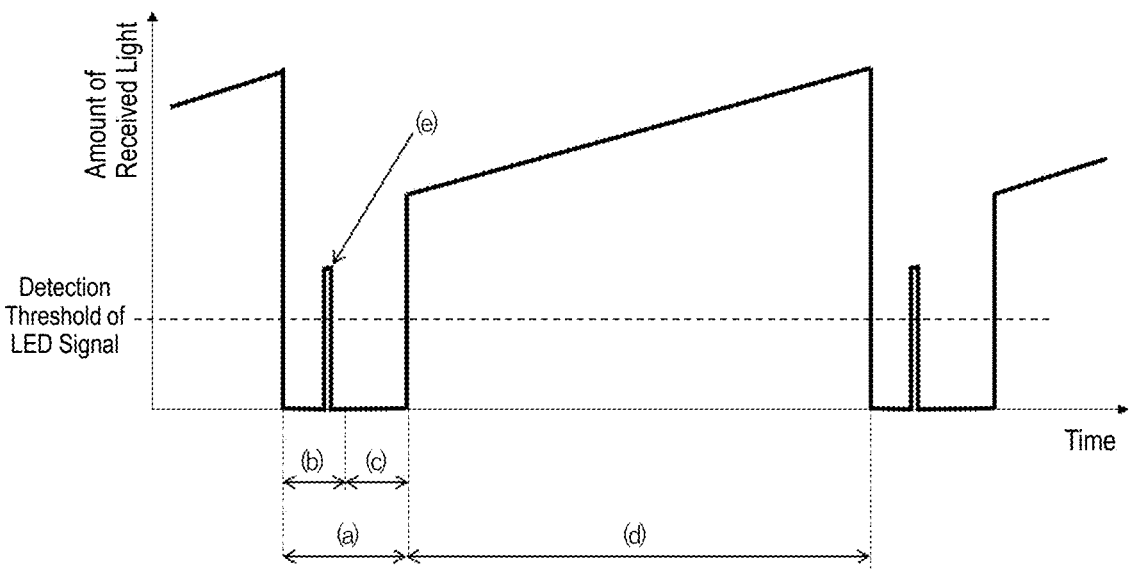
FIG. 3A is a drawing illustrating a light receiving signal waveform detected by a light receiving unit of Example 1.

The following will describe a laser gas analyzer according to embodiments with reference to the drawings.

Example 1

Figure 1:
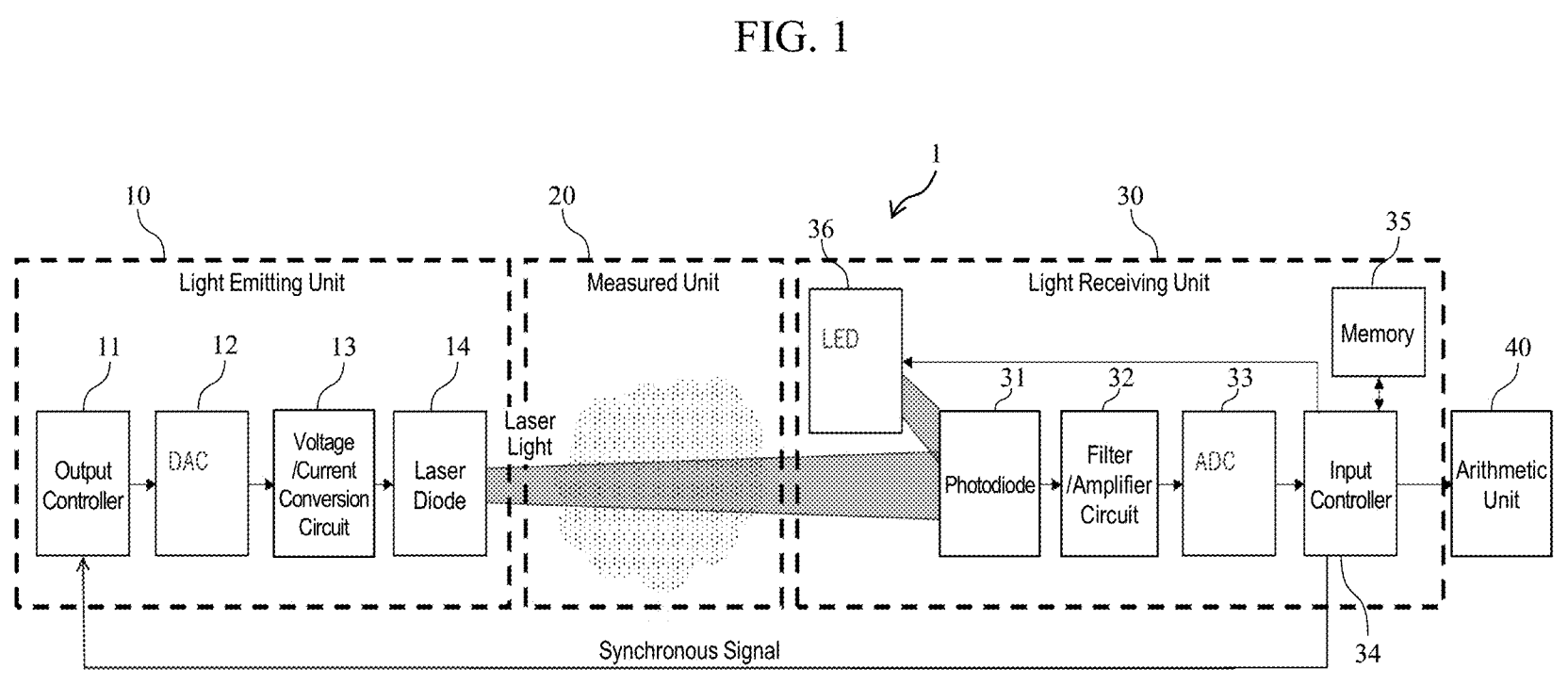

FIG. 1 is a block diagram of a laser gas analyzer of Example 1. With reference to FIG. 1, the laser gas analyzer of Example 1 will be described. A laser gas analyzer 1 is a Tunable Diode Laser Absorption Spectroscopy (TDLAS) laser gas analyzer. The laser gas analyzer 1 irradiates a measurement target gas with a laser light in a specific wavelength range, measures an amount of light of laser light that has passed through the measurement target gas, and calculates a concentration of a component contained in the measurement target gas based on an attenuation at a specific wavelength. The laser gas analyzer 1 includes a light emitting unit 10 that irradiates a laser light in a specific wavelength range, a measured unit 20 to which a measurement target gas is supplied, a light receiving unit 30 that receives a laser light that has passed through the measurement target gas, and an arithmetic unit 40 that calculates a concentration of a component contained in the measurement target gas. Note that the laser gas analyzer 1 need not include the measured unit 20. For example, in a case where the light emitting unit 10 and the light receiving unit 30 are mounted for use on a facility to which the measurement target gas of a user who uses the laser gas analyzer 1 is supplied, the laser gas analyzer 1 need not include the measured unit 20. Additionally, the arithmetic unit 40 may be a computer system built into the laser gas analyzer 1 or may be a computer system (for example, a cloud server) that can communicate with the laser gas analyzer 1.
(Light Emitting Unit 10)
The light emitting unit 10 includes an output controller 11, a Digital Analog Converter (DAC) 12, a voltage/current conversion circuit 13, and a laser diode 14. The output controller 11 generates a pattern of laser drive current in accordance with a synchronous signal from an input controller 34 in the light receiving unit 30 described later and outputs it. The DAC 12 converts the pattern (digital signal) of the laser drive current output by the output controller 11 into an analog signal and outputs it. The voltage/current conversion circuit 13 outputs the laser drive current in accordance with the analog signal output by the DAC 12. The laser diode 14 irradiates a laser light in a specific wavelength range in accordance with the laser drive current output from the voltage/current conversion circuit 13. The laser diode 14 is a first irradiation unit that irradiates the measurement target gas with laser light. The laser light irradiated by the laser diode 14 passes through the measurement target gas supplied to the measured unit 20 and is received by a photodiode 31 in the light receiving unit 30.

(Measured Unit 20)

The measurement target gas is supplied to the measured unit 20. The measurement target gas is, for example, a fuel exhaust gas and a process gas. The laser gas analyzer 1 can calculate concentrations of components, such as $O_2$, CO, $CH_4$, $CO_2$, and $NH_3$, contained in the measurement target gas.

(Light Receiving Unit 30)

The light receiving unit 30 includes the photodiode 31, a filter/amplifier circuit 32, an Analog Digital Converter (ADC) 33, the input controller 34, a memory 35, and an LED 36. The photodiode 31 receives the laser light that has been irradiated by the laser diode 14 and has passed through the measurement target gas supplied to the measured unit 20, and outputs an analog signal corresponding to the amount of light of the received laser light. The photodiode 31 is a light receiving unit that receives the laser light that has passed through the measurement target gas. The photodiode 31 is disposed so as to be opposed to the laser diode 14 in the light emitting unit 10 between which the measured unit 20 is interposed. The filter/amplifier circuit 32 filters a predetermined frequency component contained in the received analog signal and amplifies it. The ADC 33 converts the analog signal received from the filter/amplifier circuit 32 into a digital signal and outputs it. The input controller 34 performs primary arithmetic processing, such as integration processing, on the digital signal received from the ADC 33 and stores it in the memory 35. The digital signal stored in the memory 35 indicates a waveform of the amount of received light of the laser light that has passed through the measurement target gas. Hereinafter, the digital signal stored in the memory 35 is referred to as a light receiving signal waveform as appropriate.

The LED 36 is disposed on the photodiode 31 side with respect to the measured unit 20. The LED 36 is a second irradiation unit that irradiates light such that the light is received by the photodiode 31 without the light passing through the measurement target gas. The light irradiated by the LED 36 is received by the photodiode 31 without the light passing through the measurement target gas. Accordingly, even when an obstacle, such as powder dust, is present in the measurement target gas, the light irradiated by the LED 36 is received by the photodiode 31 without being affected by the obstacles. The input controller 34 controls a light emission timing of the LED 36.

The arithmetic unit 40 reads the light receiving signal waveform stored in the memory 35 and calculates the concentration of the component contained in the measurement target gas. The arithmetic unit 40 is a calculation unit that calculates the concentration of the component contained in the measurement target gas based on the amount of light of the laser light received by the photodiode 31. The arithmetic unit 40 is a computer, and includes a processor (for example, a Central Processing Unit (CPU), a field-programmable gate array (FPGA), or a Digital signal processor (DSP)), a memory (for example, a Random Access Memory (RAM)), an auxiliary storage unit (for example, a Hard Disk Drive (HDD) and a Solid State Drive (SSD)), an information output unit (for example, current output, contact output, or Ethernet communication) to an external device, a display unit, and the like. The processor, for example, reads a program for calculating the concentration from an auxiliary storage unit, loads it into a memory, and executes it. The display unit displays, for example, the calculated concentration, and the information output unit outputs, for example, the calculated concentration to the external device. Additionally, the processor reads, for example, a program for determination of presence of failure of the light receiving unit 30 from the auxiliary storage unit, loads it into the memory, and executes it.

Figure 2:
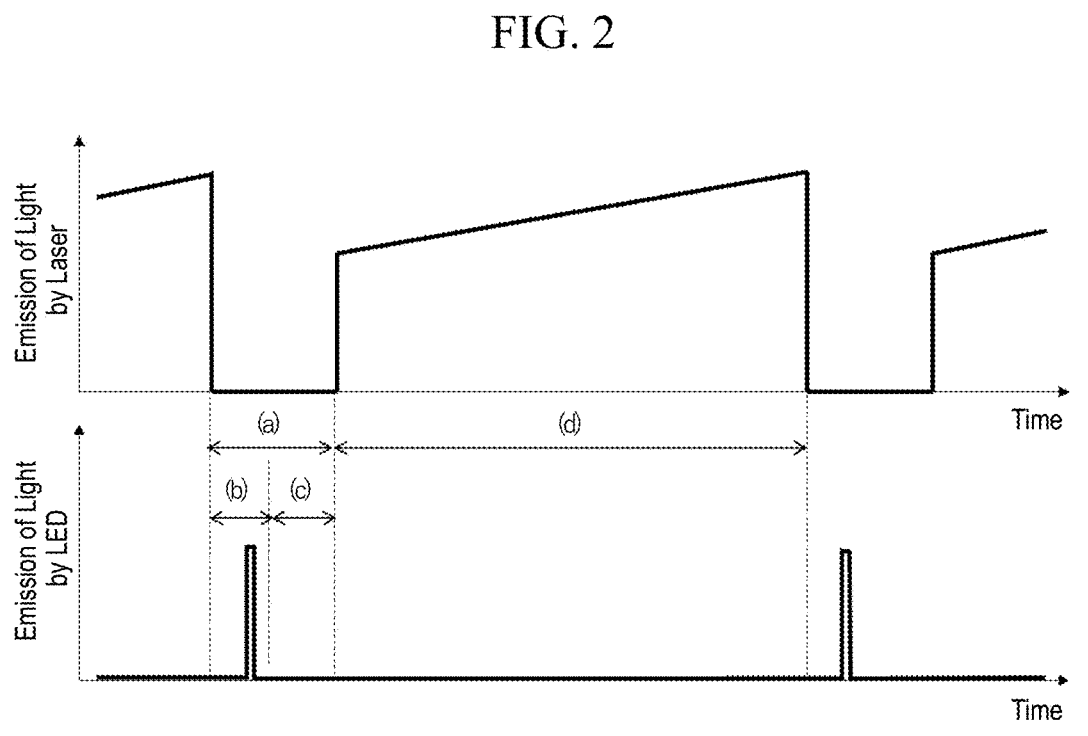

FIG. 2 is a drawing illustrating the light emission timings of a laser diode and the LED of Example 1. As illustrated in FIG. 2, a section (a period) (a) is a section in which laser light is not emitted, and a section (a period) (d) is a section in which laser light is emitted. The laser diode 14 intermittently irradiates the laser light at an interval of the predetermined section (section (a)). The section (a) is, for example, about 0.1 ms. The section (d) differs depending on the measurement target gas, and is, for example, in a range of about from 1 ms to 3 ms. The first half (b) in the section (a) is a settlement waiting section (a settlement waiting period) in which the settlement of the output of the photodiode 31 is waited for (i.e., paused), and the second half (c) is a dark current measurement section (a dark current measurement period) for measuring a dark current. That is, the first half (b) is the section not used for arithmetic operation by the arithmetic unit 40. The second half (c) is the section used to calculate a reference value of the arithmetic operation by the arithmetic unit 40. The settlement waiting section may be a predetermined time or may be a time until it is determined that a predetermined time has elapsed while the output of the photodiode 31 is under a threshold or less. The dark current measurement section is a predetermined time.

The LED 36 emits light in the settlement waiting section of the light receiving signal in the first half (b). The arithmetic unit 40 constantly observes presence of a spike signal by emission of light by the LED 36 in the light receiving signal waveform in the first half (b) to confirm soundness of the light receiving unit 30.

FIG. 3A to FIG. 3D are drawings illustrating the light receiving signal waveform of Example 1.

The light receiving signal waveform is divided into the following four patterns.

Pattern A: a pattern that includes both of a signal corresponding to the laser light irradiated by the laser diode 14 and a spike signal corresponding to the light irradiated by the LED 36 (see FIG. 3A)

Figure 3B:
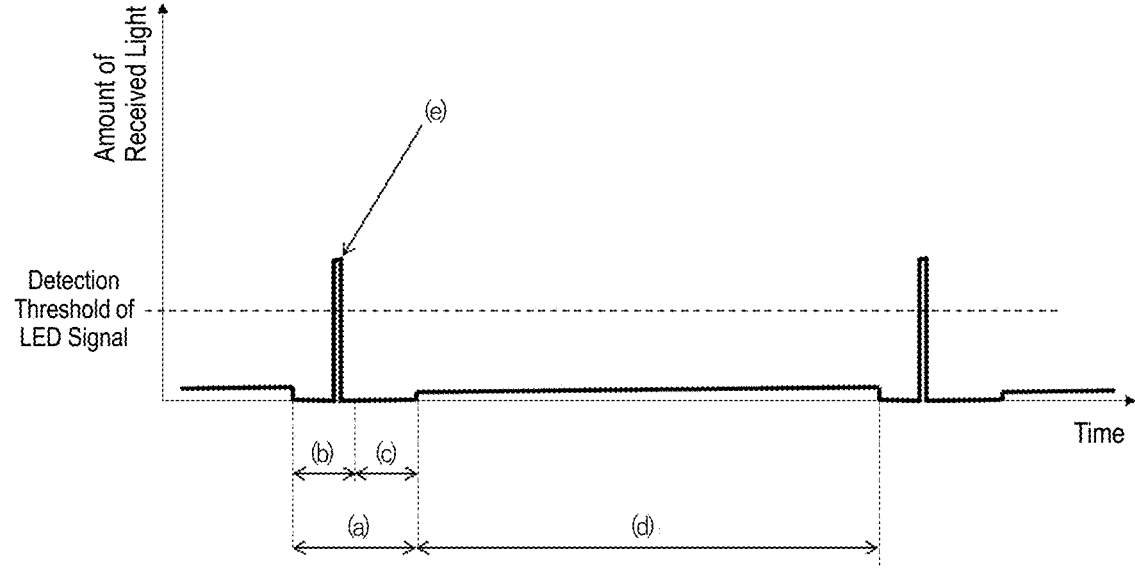
FIG. 3B is a drawing illustrating a light receiving signal waveform detected by the light receiving unit of Example 1.

Pattern B: a pattern that does not include the signal corresponding to the laser light irradiated by the laser diode 14 and includes the spike signal corresponding to the light irradiated by the LED 36 (see FIG. 3B)

Figure 3C:
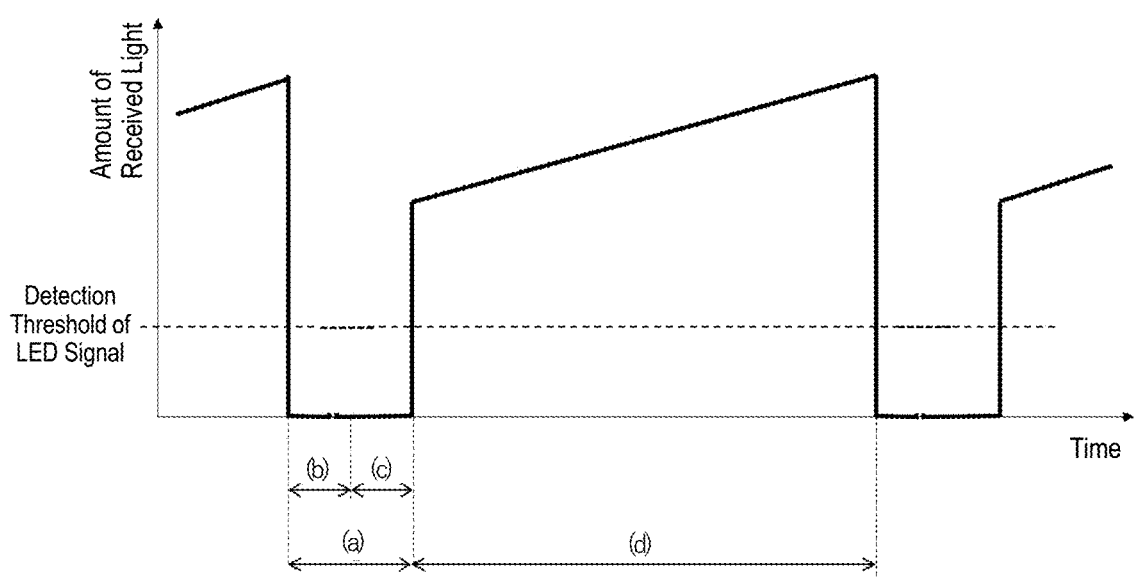
FIG. 3C is a drawing illustrating a light receiving signal waveform detected by the light receiving unit of Example 1.

Pattern C: a pattern that includes the signal corresponding to the laser light irradiated by the laser diode 14 but does not include the spike signal corresponding to the light irradiated by the LED 36 (see FIG. 3C)

Figure 3D:
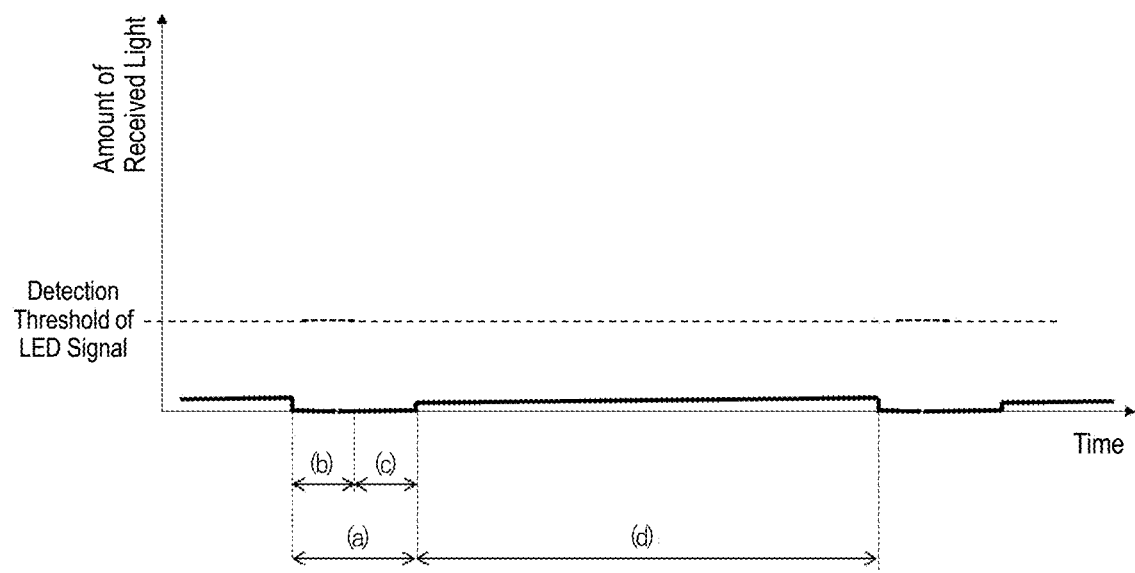
FIG. 3D is a drawing illustrating a light receiving signal waveform detected by the light receiving unit of Example 1.

Pattern D: a pattern that includes neither the signal corresponding to the laser light irradiated by the laser diode 14 nor the spike signal corresponding to the light irradiated by the LED 36 (see FIG. 3D)

The arithmetic unit 40 is an arithmetic unit that determines presence of failure of the photodiode 31 based on the output of the photodiode 31 that receives both of the laser light irradiated by the laser diode 14 and the light irradiated by the LED 36. When the arithmetic unit 40 has confirmed the light receiving signal waveform of Pattern A illustrated in FIG. 3A, the arithmetic unit 40 determines that both of the light emitting unit 10 and the light receiving unit 30 are normal. Additionally, when the arithmetic unit 40 has confirmed the light receiving signal waveform of Pattern B illustrated in FIG. 3B, the arithmetic unit 40 determines that both of the light emitting unit 10 and the light receiving unit 30 are normal. In this case, it is considered that while the signal corresponding to the laser light irradiated by the laser diode 14 cannot be confirmed, a certain amount or more of obstacles that block an optical path for laser light are present in the measurement target gas. Additionally, when the arithmetic unit 40 has confirmed the light receiving signal waveform of Pattern C illustrated in FIG. 3C, the arithmetic unit 40 determines that the light emitting unit 10 is normal while the LED 36 in the light receiving unit 30 is abnormal. When the arithmetic unit 40 has confirmed the light receiving signal waveform of Pattern D illustrated in FIG. 3D, the arithmetic unit 40 determines that the light emitting unit 10 is normal while at least one of the photodiode 31, the filter/amplifier circuit 32, or the ADC 33 in the light receiving unit 30 is abnormal. The display unit in the arithmetic unit 40 can display each of the determination results. Additionally, each of the determination results can be transmitted to the external device via the information output unit.

Effects of Example 1

The light irradiated by the LED 36 is received by the photodiode 31 without passing through the measurement target gas. Thus, the photodiode 31 can receive the light irradiated by the LED 36 without being affected by the measurement target gas. As a result, even when a certain amount or more of obstacles are present in the measurement target gas, soundness of the light receiving unit 30 can be confirmed. As a result, reliability of failure detection is increased, leading to improvement in failure detection rate. Further, the failure detection rate is an important index in terms of functional safety, and therefore it is beneficial also in terms of functional safety standard.

The input controller 34 causes the LED 36 to emit light at the predetermined timing in the settlement waiting section (the first half (b) in FIG. 2). Accordingly, using the section not used for the arithmetic operation during the usual operation in the laser gas analyzer 1, failure of the light receiving unit 30 can be determined. That is, in Example 1, without stopping the usual operation of the laser gas analyzer 1, failure of the light receiving unit 30 can be determined.

Example 2

Figure 4:
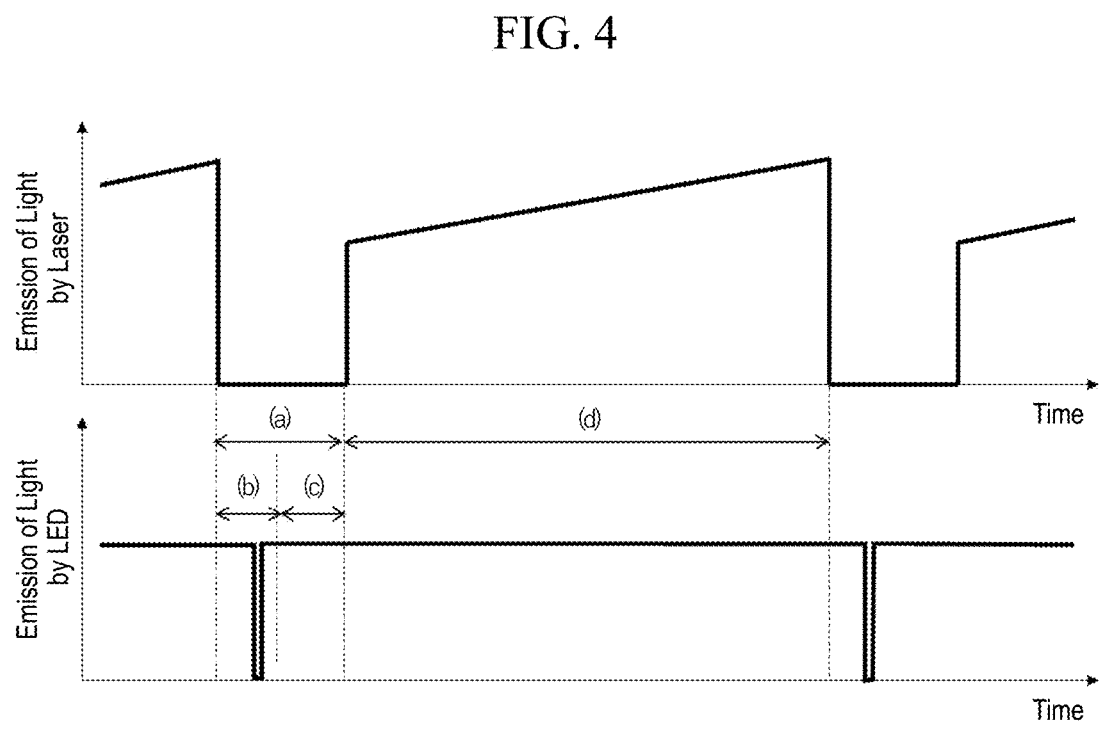

FIG. 4 is a drawing illustrating light emission timings of the laser diode and the LED of Example 2. The light emission timings of the LED 36 are inverted between Example 1 and Example 2. In Example 1, the LED 36 irradiates light at the predetermined timing in the settlement waiting section (b) of the light receiving signal. In Example 2, the LED 36 turns off at the predetermined timing (stops irradiating the light during a stop period) in the settlement waiting section (b) of the light receiving signal. In Example 2, the LED 36 constantly irradiates light in the section other than the predetermined timing (the stop period). In the first half (b), the arithmetic unit 40 constantly observes whether a negative spike signal by turning off the LED 36 is present in the light receiving signal waveform to confirm soundness of the light receiving unit 30.

Effects of Example 2

By constantly causing the LED 36 to emit light in the section other than the predetermined timing, an amount of offset light due to emission of light by the LED 36 is added to the amount of received light of the photodiode 31. By adjusting the amount of light of the light irradiated by the LED 36, the photodiode 31 can receive the laser light and perform output in the range where accuracy of the output with respect to the input of the photodiode 31 is high. Consequently, the photodiode 31 can output the value at high accuracy with respect to the received laser light. Since the other effects are similar to those of Example 1, the description thereof will be omitted.

Example 3

Figure 5:
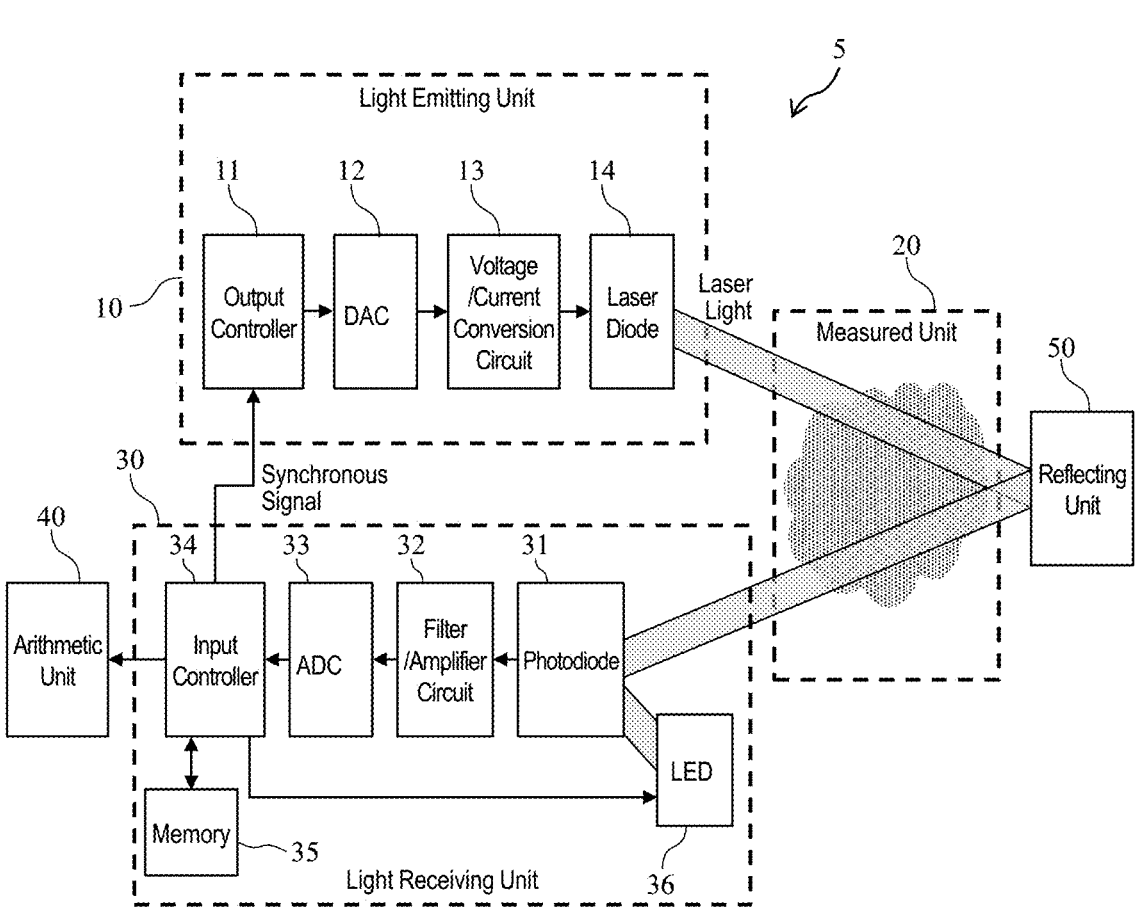
FIG. 5 is a block diagram of a laser gas analyzer of Example 3.

FIG. 5 is a block diagram of a laser gas analyzer of Example 3. With reference to FIG. 5, a laser gas analyzer 5 of Example 3 will be described. Similarly to the laser gas analyzer 1 of Example 1, the laser gas analyzer 5 of Example 3 includes the light emitting unit 10, the measured unit 20, the light receiving unit 30, and the arithmetic unit 40. The measured unit 20 of the laser gas analyzer 5 is a probe that retrieves the measurement target gas. Additionally, the laser gas analyzer 5 includes a reflecting unit 50 that reflects laser light. The laser light irradiated by the laser diode 14 passes through a gas supplied to the measured unit 20 and is reflected by the reflecting unit 50. The reflected laser light is received by the photodiode 31. The light emitting unit 10 and the light receiving unit 30 of Example 3 are disposed on the same side with respect to the measured unit 20.

Effects of Example 3

The laser gas analyzer 5 including the probe type measured unit 20 allows obtaining the effects similar to those of Example 1.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

For example, the number of the LEDs 36 of Examples 1 to 3 is one, but may be two or more.

Additionally, the LEDs 36 of Examples 1 to 3 may be another luminous body, such as a laser diode, and may be able to change an amount of light and a wavelength of the light irradiated by the luminous body. By changing the amount of light and the wavelength of the light irradiated by the luminous body and evaluating the change in the amount of light detected by the photodiode 31, soundness and performance of the photodiode 31 can be evaluated. The above-described change in the wavelength may be achieved by a combination of turning on and turning off lights of a plurality of luminous bodies.

Additionally, when the laser gas analyzers of Examples 1 to 3 have an Auto Gain function, it is preferred that the Auto Gain function does not work on a pulse signal by the LED 36.

Moreover, when the LED 36 is constantly lit as in Example 2, use of AC coupling is preferred.

Additionally, in Examples 1 to 3, failure of the light receiving unit 30 is determined using the settlement waiting section. However, for example, it is only necessary to prepare a failure diagnosis mode for the laser gas analyzer and emit lights of the photodiode 31 and the LED 36 in the failure diagnosis mode.

Comparative Example

Figure 6:
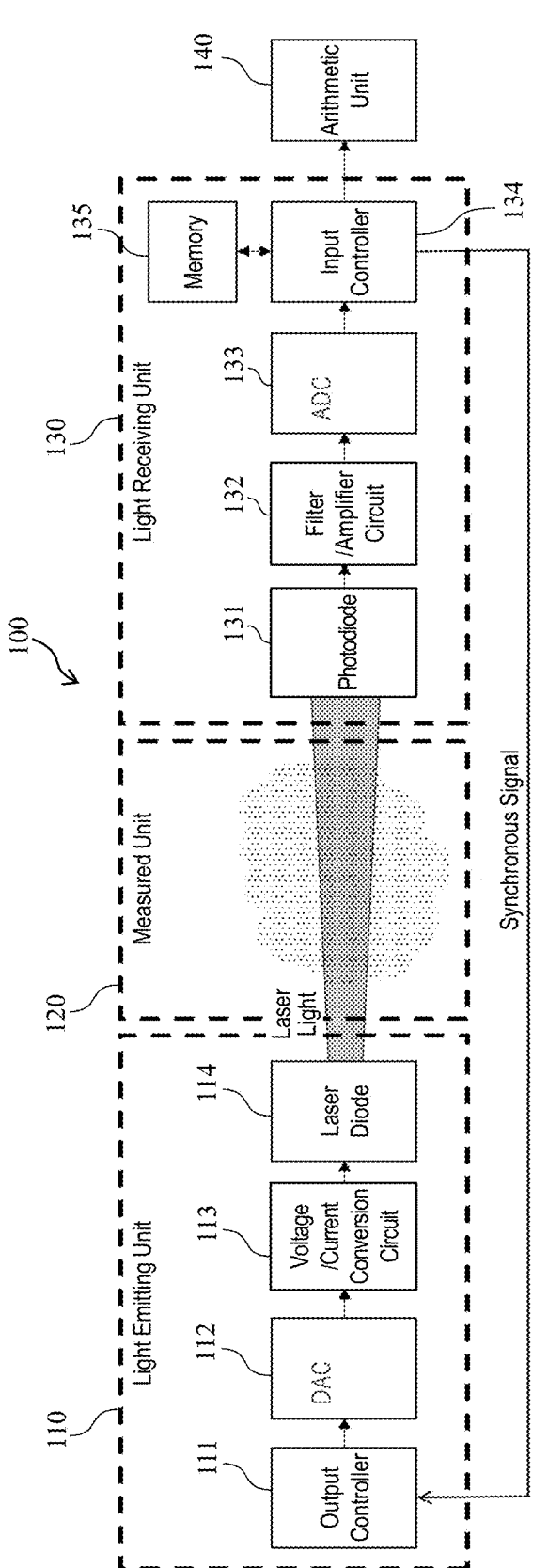
FIG. 6 is a block diagram of a laser gas analyzer of Comparative Example.

FIG. 6 is a block diagram illustrating a laser gas analyzer of Comparative Example. With reference to FIG. 6, a circuit configuration and an operation of a laser gas analyzer 100 of Comparative Example will be described.

In a light emitting unit 110, an output controller 111 receives a synchronous signal from an input controller 134 in a light receiving unit 130 and generates a pattern of laser drive current. The pattern is supplied as drive current to a laser diode 114 via a Digital Analog Converter (DAC) 112 and a voltage/current conversion circuit 113. Thus, the laser diode 114 irradiates laser light. The laser light after passing through the measurement target gas is detected by a photodiode 131 in the light receiving unit 130. The output of the photodiode 131 is input to the input controller 134 via a filter/amplifier circuit 132 and an Analog Digital Converter (ADC) 133. The input controller 134 sequentially stores the output of the photodiode 131 in a memory 135. An arithmetic unit 140 reads the output of the photodiode 131 stored in the memory 135 and calculates a concentration value.

Figure 7:
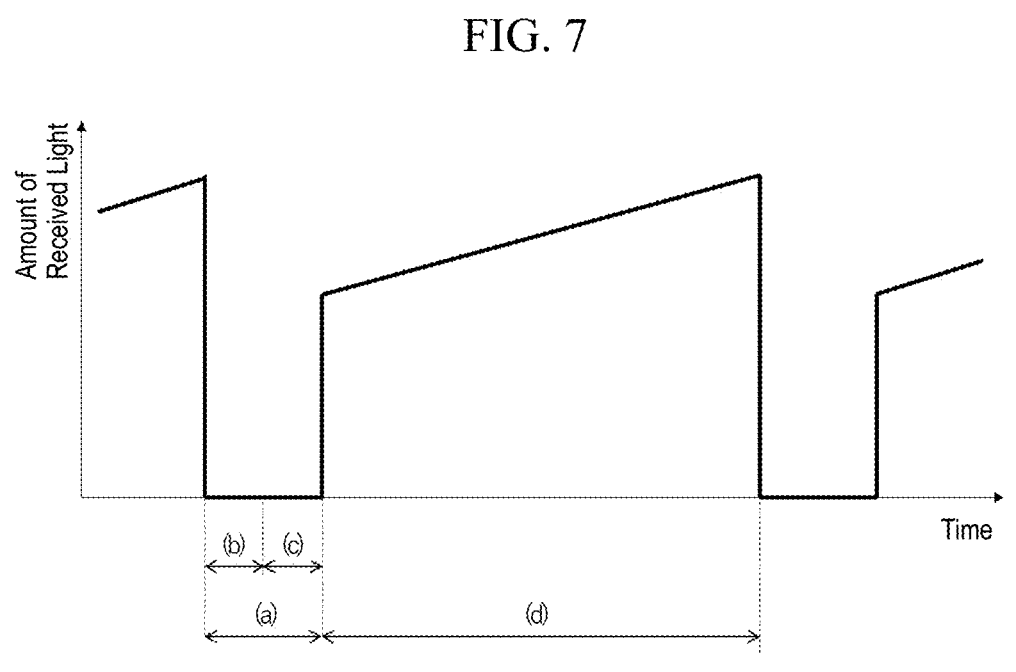

FIG. 7 is a drawing illustrating a light receiving signal waveform detected by the laser gas analyzer of Comparative Example. The light emission timing of the laser light will be described with reference to FIG. 7. In FIG. 7, a section (a) is a section in which laser light is not emitted, and a section (d) is a section in which laser light is emitted. Emission and no emission of the laser light are alternately repeated.

Next, a method for failure diagnosis of the photodiode 131, the filter/amplifier circuit 132, and the ADC 133 in the light receiving unit 130 in the laser gas analyzer 100 of Comparative Example will be described. When any of the photodiode 131, the filter/amplifier circuit 132, and the ADC 133 has failure, there is a high possibility of the output value of the ADC 133 fixed to a certain constant value. Therefore, in the laser gas analyzer 100 of Comparative Example, when the variation of the output of the ADC 133 is in a constant range, it is determined that the light receiving unit 130 (any of the photodiode 131, the filter/amplifier circuit 132, and the ADC 133) has failure.

However, not only the case where any of the photodiode 131, the filter/amplifier circuit 132, and the ADC 133 has failure, but also the case where a certain amount or more of an obstacle, such as powder dust, blocking the optical path for laser light is present in the measurement target gas, the variation of the output of the ADC 133 possibly is in a constant range. Accordingly, in the method for failure diagnosis of Comparative Example, the case where a certain amount or more of an obstacle, such as powder dust, blocking the optical path for laser light is present in the measurement target gas, it is determined as failure of the light receiving unit 130, and therefore the failure of the light receiving unit 130 was not able to be accurately determined.

DESCRIPTION OF SYMBOLS

1 Laser gas analyzer
10 Light emitting unit

11 Output controller
12 DAC
13 Voltage/current conversion circuit
14 Laser diode
20 Measured unit
30 Light receiving unit
31 Photodiode
32 Filter/amplifier circuit
33 ADC
34 Input controller
35 Memory
36 LED
40 Arithmetic unit
50 Reflecting unit

What is claimed is:

1. A laser gas analyzer comprising:
a laser diode that irradiates a measurement target gas with laser light;
a light receiving unit including:
a photodiode that receives the laser light that has passed through the measurement target gas; and
a light emitting diode (LED) that irradiates LED light such that the LED light is received by the photodiode without passing through the measurement target gas; and
a processor that:
calculates a concentration of a component contained in the measurement target gas based on an amount of light of the laser light received by the photodiode, and
determines presence of failure of the photodiode based on an output of the photodiode that receives both of the laser light and the LED light, wherein
the laser diode intermittently irradiates the laser light,
the LED irradiates the LED light at a predetermined timing during a period in which the laser diode does not irradiate the laser light,
when the processor detects the LED light but not the laser light during the period, the processor determines that the light receiving unit is normal, and
when the processor does not detect either the laser light or the LED light during the period, the processor determines that at least the light receiving unit is abnormal.

2. The laser gas analyzer according to claim 1, wherein the period includes:
a settlement waiting period during which settlement of an output of the photodiode is paused; and
a dark current measurement period for measuring a dark current, and
the LED irradiates the LED light during the settlement waiting period.

3. The laser gas analyzer according to claim 1, wherein the LED changes at least one of an amount of light of the LED light or a wavelength of the LED light.

* * * * *